United States Patent [19]

Kane

[11] Patent Number: 4,785,814

[45] Date of Patent: Nov. 22, 1988

[54] OPTICAL PROBE FOR MEASURING PH AND OXYGEN IN BLOOD AND EMPLOYING A COMPOSITE MEMBRANE

[75] Inventor: James Kane, Miami, Fla.

[73] Assignee: Cordis Corporation, Miami, Fla.

[21] Appl. No.: 84,301

[22] Filed: Aug. 11, 1987

[51] Int. Cl.[4] .............................................. A61B 5/00
[52] U.S. Cl. ................................... 128/634; 128/665; 356/41
[58] Field of Search ......................... 356/41, 411, 412; 128/634, 670, 665; 250/458.1; 422/58

[56] References Cited

U.S. PATENT DOCUMENTS 4,200,110  4/1980  Peterson et al. ..................... 128/634
4,476,870  10/1984 Peterson et al. ................. 128/665 X
4,560,248  12/1985 Cramp et al. .................... 356/412 X
4,712,865  12/1987 Hsu et al. .......................... 350/96.29

Primary Examiner—William E. Wayner
Attorney, Agent, or Firm—Tarolli, Sundheim & Covell

[57] ABSTRACT

An optical probe is presented for use in measuring pH and oxygen content in blood in a blood vessel within a living body. An elongated flexible optical fiber means is provided which has a proximal end and a distal end. The distal end is adapted to be inserted into a blood vessel. A membrane is secured to the distal end of the optical fiber and receives light from the distal end of the fiber and returns light therethrough to the proximal end. The membrane is constructed of hydrophilic porous material containing a pH sensitive dye. A plurality of microspheres are embedded in and carried by the membrane. These microspheres are constructed hydrophobic material and each carries a fluorescent dye quenchable with oxygen. Consequently, when light is supplied to the proximal end of the optical fiber, it is conveyed to the membrane. This causes the pH sensitive dye to react and light is conveyed through the optical fiber having an intensity level indicative of the pH level in the blood. The oxygen sensitive dye fluoresces and light is transmitted to the proximal end of an intensity which varies with the partial pressure of oxygen.

9 Claims, 1 Drawing Sheet

OPTICAL PROBE FOR MEASURING PH AND OXYGEN IN BLOOD AND EMPLOYING A COMPOSITE MEMBRANE

BACKGROUND OF THE INVENTION

This invention relates to the art of measuring blood parameters and more particularly pH and oxygen present in blood.

In a critical care setting, there is a need for measurement of various blood parameters. Included among these parameters are pH and oxygen. The values of these parameters are used in patient management. For example, both the pH content and the oxygen content are important parameters in the study of blood oxygen content. pH is an important parameter in studying some diseases such sickle cell anemia. Oxygen content is also an important parameter in the study of sickle cell anemia.

Both pH and oxygen blood parameters have been studied in the past by external means, wherein blood samples are withdrawn from a patient and studied externally of the body. However, there is concern in critically ill patients that blood withdrawal, even in small amounts, could present problems to a patient. Moreover, it is frequently desirable in studying such diseases as sickle cell anemia that an analysis be made in place during exercise.

It has been known to provide devices for use during in-dwelling measurement of various blood parameters. For example, U.S. Pat. No. 3,787,119 to Tybak discloses a catheter having a microlamp and a photosensitive element and other elements including a cup-like element for use in receiving blood and providing electrical output signals by means of wires extending through the catheter. Such construction could well present size limitations as well as stiffness limitations of the sensor carrier or catheter employed for incorporating suitable sensor wires.

The U.S. Pat. No. 3,814,081 to Morie discloses an optical measuring catheter employing fiber optic means for use in measuring oxygen saturation in blood, as well as blood pressure.

Whereas Rybak and Morie employ teachings of in-dwelling catheters which may be employed for measuring a plurality of blood parameters, there is no teaching of a device which can be employed for measuring both partial pressure of oxygen (PO$_2$) as well as pH content of blood.

The U.S. Pat. No. 4,200,110 to Peterson et al. discloses a fiber optic pH probe wherein the probe includes an ion permeable membrane which encloses a guide containing solid material comprised of a hydrophilic copolymer having a pH sensitive dye attached thereto. The probe operates on the concept of optically detecting a change in color of the pH sensitive dye when excited by light. A phenol red dye is employed so that it absorbs light at a particular wavelength, on the order of 550 nm, with the amount of light being absorbed varying in dependence upon the pH level. There is no teaching, then, as to how the probe may also be employed for measuring oxygen partial pressure (pO$_2$).

The U.S. patent to Peterson et al. U.S. Pat. No. 4,476,870 discloses a fiberoptic oxygen partial pressure (pO$_2$) probe. This probe includes a hydrophobic gas permeable envelope which contains an adsorptive support which contains a fluorescent dye. Use of the probe for measuring partial pressure of gaseous oxygen in the bloodstream is based on the principle of dye fluorescent oxygen quenching. Thus, with the probe in place within a bloodstream, fluorescent dye is excited by light of a blue wavelength causing the dye to fluoresce at a green wavelength with the intensity of emitted light decreasing (quenching) with increasing levels of the partial pressure of gaseous oxygen in the bloodstream. There is no teaching in Peterson U.S. Pat. No. 4,476,870 of employing the same probe to also measure the pH content of the blood.

There is no teaching in the two Peterson patents, supra, by which features of the two probes could be combined together to provide a single probe for measuring pH and oxygen partial pressure with a single probe either simultaneously or in sequence. For example, if one employs the hydrophilic material containing the pH sensitive dye of Peterson U.S. Pat. No. (4,200,110) within the hydrophobic envelope in Peterson U.S. Pat. No. (4,476,870), the resultant probe would not be effective to sense pH content.

SUMMARY OF THE INVENTION

It is an object of the present invention to provide a fiberoptic sensitive probe which may be employed for sensing both pH and oxygen partial pressure either simultaneously or in sequence without having to remove the probe from its in-dwelling location within a blood vessel.

It is a still further object of the present invention to provide such an improved fiberoptic probe employing an improved composite membrane constructed of hydrophilic material containing hydrophobic microspheres therein with the former containing pH sensitive dye and the latter containing oxygen quenching dye.

In accordance with the present invention, there is provided an improved optical probe for use in measuring both pH and oxygen in a blood vessel within a living body. The probe includes an elongated flexible optical fiber having a proximal end and a distal end and adapted to be inserted into a blood vessel. The optical fiber serves to permit transmission of light between the proximal and distal ends thereof. A composite membrane is secured to the distal end of the optical fiber for use in receiving light therefrom and returning light thereto. The membrane is constructed of hydrophilic porous material with pH sensitive dye carried thereby. A plurality of microspheres constructed of hydrophobic material are embedded within and carried by the membrane. The microspheres carry a fluorescent dye quenchable in the presence of oxygen. Consequently, when exciting light is supplied to the proximal end and conveyed to the membrane, the pH sensitive dye will fluoresce and emit light at an intensity level depending upon the pH level in the blood, whereas the oxygen quenching dye will fluoresce and emit light, the intensity level varying inversely with that of the partial pressure of oxygen.

BRIEF DESCRIPTION OF THE DRAWINGS

The foregoing and other objects and advantages of the present invention will become more readily apparent from a consideration of the following description as taken in conjunction with the accompanying drawings, wherein.

DETAILED DESCRIPTION OF THE PREFERRED EMBODIMENT

Figure 1:
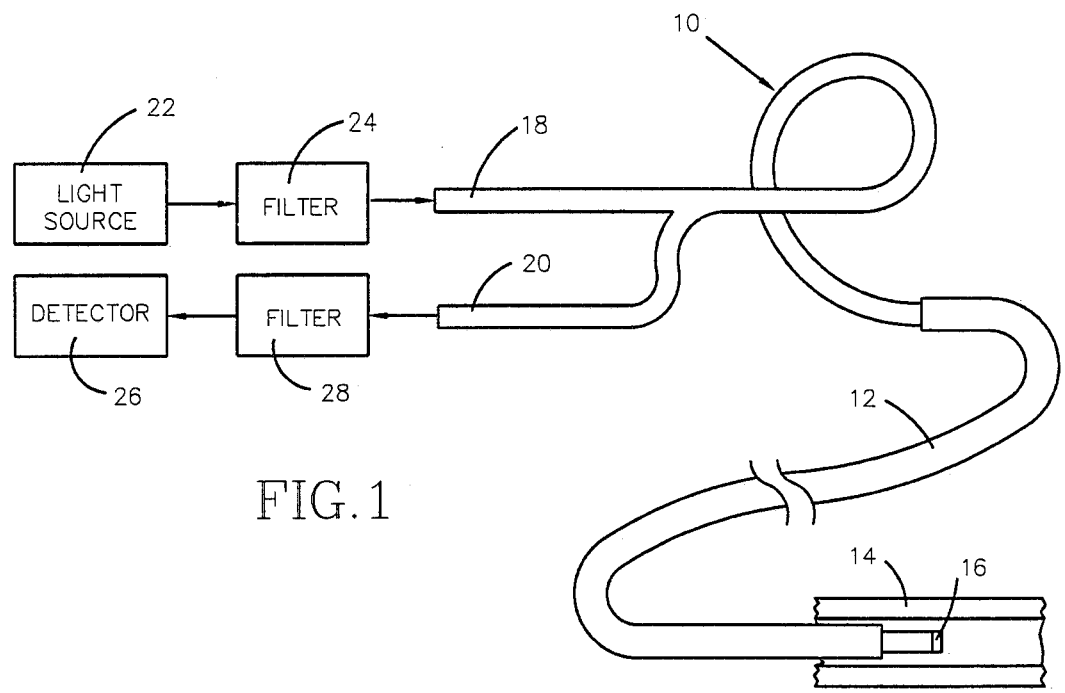
FIG. 1 is a schematic illustration of the optical probe in conjunction with one application of this invention.

Reference is now made to the drawings wherein the showings are for purposes of illustrating a preferred embodiment only, and not for limiting same. FIG. 1 illustrates an application of the invention as applied to the measurement of oxygen partial pressure and pH content of blood within a patient's blood vessel and includes an optical fiber 10 which extends through an elongated single lumen catheter 12, the distal end of which may be inserted into a patient's blood vessel 14 and advanced to a site at which measurements are to be made. The optical fiber 10 may be carried by the catheter during the insertion into the blood vessel or, alternatively, once the distal end of the catheter is in place, the optical fiber 10 may be inserted and advanced through the lumen of the catheter. The distal end of the optical fiber may be advanced beyond the distal end of the catheter, as is shown in FIG. 1, while measurements are being made. A composite membrane 16, to be discussed in greater detail hereinafter, is secured to the distal end of the optical fiber and is employed in the measurement of oxygen partial pressure and pH content.

The optical fiber 10 is bifurcated at its proximal end defining two legs 18 and 20. Leg 18 is positioned to receive light from a light source 22 by way of a suitable filter 24 for transmission to the composite membrane 16. As will be described in greater detail hereinafter, the membrane 16 responds to changes in fluoresce and/or absorption of light in the presence of blood and this information is returned in the light signal returning to the proximal end of the optical fiber and is conveyed by leg 20 to a detector 26 by way of a suitable filter 28.

As shown in FIG. 1, the optical fiber 10 is looped at least once prior to insertion into the proximal end of catheter 12. This is done to enhance light distribution throughout the fiber. The catheter 12 may suitably take the form of a single lumen, thin walled catheter, such as that provided by Cordis Corporation, and known as Cordis FR5 thin walled catheter. This catheter may have a diameter on the order of 0.066 inches and is constructed of plastic material, such as polyurethane.

The optical fiber 10 may take various forms well known in the art and, for example, may take the form of a silica core having a core diameter on the order of 368 micrometers. The core is covered with a cladding, which may also be of silica, and with a clad diameter on the order of 400 micrometers, nominally. Other optical fibers may be used, such as one having a polymethymethacrylate core and a fluorocarbon cladding. Also, the optical fiber used may not be confined to one with a core cladding construction, but may be a step index fiber or a graded index fiber.

Figure 2:
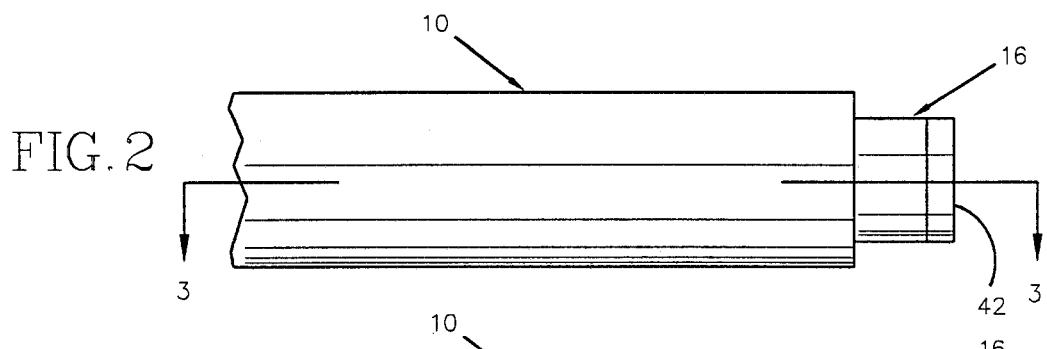
FIG. 2 is an enlarged view of the distal end of the optical probe.
Figure 3:
FIG. 3 is an enlarged longitudinal section of the distal end of the optical probe taken along line 3—3, looking in the direction of the arrows of FIG. 2, but with the end placed mirror removed.

Attention is now more particularly directed to FIGS. 2 and 3, which illustrate the optical probe in greater detail. As shown there, the composite membrane 16 is mounted to the distal end of the cladded optical fiber 10. Membrane 16 is preferably constructed of hydrophilic material in which microspheres 40 of hydrophobic material are carried. Hydrophilic materials which may be employed for the membrane 16 include hydroxyethyl methacrylate (HEMA) and polyacrylamide. The hydrophilic membrane preferably contains a pH sensitive dye of the type which will fluoresce when excited by light. A suitable fluorescent dye for pH is fluorescein. The pH content may be measured by either fluorescence or absorbance of light. Whereas this embodiment prefers measurement by fluorescence, it is contemplated that the pH measurement may be obtained by absorbance. In which case, it may be necessary to employ a mirror 42 at the distal end, as is illustrated in FIG. 2 (but not in FIG. 3). Examples of absorbance dyes for measuring pH include phenol red and brilliant yellow.

The hydrophobic microspheres 40 dispersed throughout the hydrophilic membrane 16 may be constructed of such hydrophobic materials as silastic, poly (acrylates), polystrene, or rubber (natural or synthetic). These hydrophobic microspheres contain oxygen quenchable fluorescent dyes. Such dyes include 9, 10 diphenyl anthracene, or rubrene, perylene, and decacyclene. In constructing the optical probe as illustrated in FIGS. 2 and 3, the membrane may be attached to the distal end of the optical fiber 10 by applying the membrane to the fiber tip in the following manner. The membrane may initially take the form of a liquid monomer into which microspheres 40 are dispersed. The microspheres are filled with the oxygen quenchable fluorescent dye, as with the use of a swelling agent. With the distal end of the optical fiber in contact with the monomer, the monomer is then exposed to light causing it to polymerize. The hydrophilic membrane preferably contains a pH sensitive dye of the type that will fluoresce and such a fluorescent dye, as discussed above, may be fluorescein.

With the optical probe in place for sensing pH and oxygen within a blood vessel, such as vessel 14, the operator will energize a suitable polychromatic light source 122. A filter 24 may be employed so that the excitation light is at a wavelength on the order of 480 nm. It has been determined that light at this wavelength will excite the pH sensitive dye, causing it to fluoresce at a wavelength on the order of 520 nm. The intensity of this light will decrease with the level of pH content in the blood being examined. The emitted light will then be passed by the optical fiber 12 from the distal end to the proximal end thereof and will be directed by leg 20 to the filter 28, which, in this example, serves to pass light at a wavelength on the order of 520 nm. The detector 26, which may take any suitable form, responds to the intensity of the received light for providing a readout indicative of the pH content of the blood. The operator may then test the blood for the oxygen concentration, and this may be done by employing a substitute filter for filter 24 which will pass light having a wavelength on the order of 375 nm. It has been determined that light at this wavelength will excite the fluorescent dye in the hydrophobic microspheres so that it fluoresces and emits light at a wavelength on the order of 430 nm. However, the intensity of this emitted light is quenched or diminished by oxygen. The emitted light is transmitted from the distal end to the proximal end of the optical fiber and is directed by leg 20 to a filter 28. At this time, the filter 28 is chosen so as to pass light at a wavelength on the order of 430 nm. This is detected by detector 26 which provides an output indication representative of the partial pressure of oxygen.

In the embodiment described thus far, the pH content is measured by fluorescence. As previously discussed, it may also be measured by absorbance. In which case, an absorbance dye for pH will be employed. Also, to assist in detecting the amount of light that has been absorbed, a mirror 42 is used on the distal end of the optical probe. The mirror may take the form of a flat hemispheric of parabolic surface. The surface of the mirror adjacent to the membrane is preferably aluminized or of sputtered aluminum. This will help reflect light back into the optical fiber for transmission to the proximal end. Again, the excitation light is on the order of 480 nm so that a filter 24 for passing light at this wavelength is employed.

Figure 4:
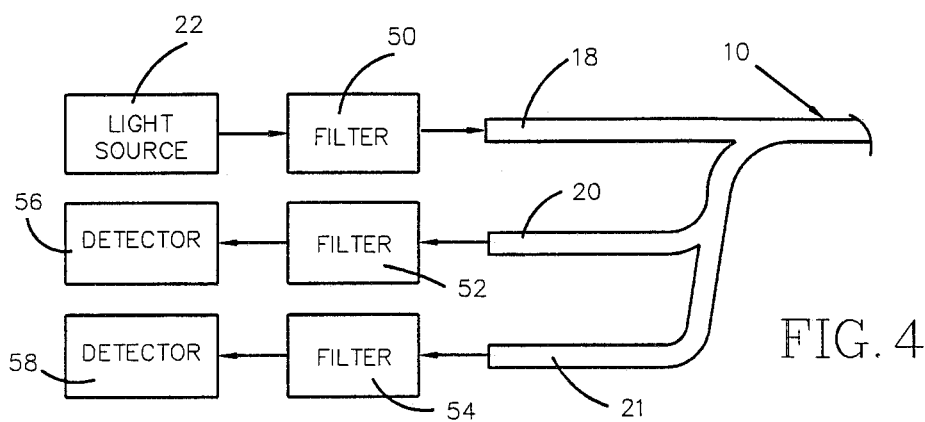
FIG. 4 is another illustration similar to that of FIG. 1 showing a still further application of the present invention.

Reference is now made to the embodiment illustrated in FIG. 4 which serves to excite the pH sensitive dye as well as the oxygen quenchable dye with light at the same wavelength. Thus, in this embodiment, the operator may turn on the polycromatic light source 22 which supplies light into leg 18 at the proximal end of the optical fiber 10 by way of a filter 50. In this embodiment, the filter 50 serves to pass light having a wavelength on the order of 480 nm. It has been determined that light at this wavelength will excite the fluorescent dye used for pH so that the dye will fluoresce and emit light at a wavelength on the order of 525 nm. Additionally, it has been determined that light at this wavelength will excite the oxygen quenchable fluorescent dye in the microspheres so as to fluoresce and emit light at a wavelength on the order of 600 nm. A mirror is not required in this embodiment, since absorbance is not being employed for measuring pH content.

With the optical fiber in place within the blood vessel, the operator may turn on the light source 22 so that light is passed by way of the optical fiber to the optical probe. The pH sensitive dye and the oxygen quenchable fluorescent dye will be excited and emit light in their respective wavelengths. Light emitted from these dyes is returned to the proximal end of the optical fiber, which has been modified so as to include an additional bifurcated leg 21 so that leg 20 is employed for directing light to a filter 52 whereas leg 21 is employed for directing light to a filter 54. Filter 52 is chosen so as to pass light emitted from the pH sensitive dye with this light being on the order of 525 nm, whereas filter 54 is chosen so as to pass light emitted from the oxygen quenchable fluorescent dye and this is on the order of 600 nm. A suitable detector 56 receives the light passed by filter 52 and provides an output indication representative of the pH content of the blood. Similarly, a detector 58 receives light passed by filter 54 and provides a suitable output indicative of the partial pressure of oxygen in the blood.

Although the invention has been described in conjunction with preferred embodiments, it is to be appreciated that various modifications may be made without departing from the spirit and scope of the invention as defined by the appended claims.

Having described preferred embodiments of the invention, I claim:

1. An optical probe for use in measuring pH and oxygen in blood within a blood vessel of a living body, comprising:
   an elongated, flexible optical fiber means having a proximal end and a distal end with said distal end adapted to be inserted into a said blood vessel;
   membrane means secured to said distal end of said optical fiber means for receiving light from the distal end thereof and returning light therethrough to the proximal end thereof; and
   said membrane means being constructed of hydrophilic porous material, pH sensitive dye carried by said porous material, a plurality of microspheres constructed of hydrophobic material embedded in and carried by said membrane means, said microspheres carrying a fluorescent dye quenchable with oxygen, whereby light supplied to said proximal end is conveyed to said membrane means causing the pH sensitive dye to react to the light and transmit light back to the proximal end thereof at an intensity level dependent upon the pH level in the blood and causing the oxygen sensitive dye to fluoresce and emit light varying in intensity as a function of the partial pressure of oxygen in the blood with the emitted light transmitted through said optical means to the proximal end thereof.

2. An optical probe as set forth in claim 1 wherein said pH sensitive dye is a fluorescent dye whereby when light is supplied to said membrane means the pH sensitive dye will flouresce and emit light, the intensity of which varies in dependence upon the pH level in said blood.

3. An optical probe as set forth in claim 2 wherein said pH fluorescent dye is fluorescein.

4. An optical probe as set forth in claim 1 wherein said pH sensitive dye is an absorbance dye whereby when light is supplied to said membrane means the pH sensitive absorbance dye will absorb light with the amount of light absorbed being dependent upon the pH level in said blood.

5. An optical probe as set forth in claim 4 wherein said absorbance dye is selected from a group consisting of phenol red and brilliant yellow.

6. An optical probe as set forth in claim 1 wherein said oxygen quenchable fluorescent dye is selected from a group consisting of 9,10-diphenyl antracene, rubrene, perylene and decacyclene.

7. An optical probe as set forth in claim 2 including means for supplying light to the proximal end of said optical fiber means with said light exhibiting a wavelength on the order of 480 nm causing said pH fluorescent dye to fluoresce and emit light at a wavelength on the order of 525 nm for transmission through said optical fiber means to the proximal end thereof, and detector means including filtering means for receiving light from the proximal end at a wavelength on the order of 525 nm for providing an output indication representative of the pH content of the blood.

8. An optical probe as set forth in claim 2 including light source means for transmitting light to the proximal end of said optical fiber means at a wavelength on the order of 375 nm for transmission to said membrane means for causing the fluorescent dye within said microspheres to fluoresce and emit light at a wavelength on the order of 430 nm with the intensity thereof being quenched in dependence upon oxygen content with the emitted light being transmitted by said optical fiber means to the proximal end thereof, and detector means including filter means for receiving said emitted light at a wavelength on the order of 430 nm for providing an output indication representative of the partial pressure of oxygen in said blood.

9. An optical probe as set forth in claim 2 including light source means for transmitting light to the proximal end of said optical fiber means at a wavelength on the order of 480 nm which causes the pH sensitive fluorescent dye to fluoresce and emit light at a wavelength on the order of 525 nm and simultaneously causes the fluorescent dye in said microspheres to fluoresce and emit light on the order of 600 nm with the intensity thereof being quenchable in the presence of oxygen, detector means for receiving light from the proximal end of said optical fiber means and including a first filter for passing light exhibiting a wavelength on the order of 525 nm and a first detector means responsive to the filtered light at said wavelength of 525 nm for providing an output indication representative of the pH content of the blood, and second filter means for passing light having a wavelength on the order of 600 nm and second detector means for receiving filtered light on the order of 600 nm and providing an output indication representative of the partial pressure of oxygen.

* * * * *